(12) United States Patent
Wilmot et al.

(10) Patent No.: US 6,210,369 B1
(45) Date of Patent: Apr. 3, 2001

(54) AUTOMATIC INJECTOR

(75) Inventors: John G. Wilmot, Mount Airy; Jeffrey L. Goldberg, Olney, both of MD (US); Jon Page, Broomfield, CO (US); Cliff Ketcham, Boulder, CO (US); Jeffrey P. Castleberry, Longmont, CO (US); Jason Morton, Loveland, CO (US); Dave Edsall, Louisville, CO (US); Robert R. Boyd, Boulder, CO (US); Robert L. Hill, Abingdon, MD (US)

(73) Assignee: Meridian Medical Technologies Inc., Columbia, MD (US)

( * ) Notice: Subject to any disclaimer, the term of this patent is extended or adjusted under 35 U.S.C. 154(b) by 0 days.

(21) Appl. No.: 09/212,570

(22) Filed: Dec. 16, 1998

Related U.S. Application Data

(60) Provisional application No. 60/069,775, filed on Dec. 16, 1997.

(51) Int. Cl.[7] ..................................................... A61M 5/20
(52) U.S. Cl. ........................... 604/157; 604/201; 604/197
(58) Field of Search ..................................... 604/201, 204, 604/156, 157, 232, 197

(56) References Cited

U.S. PATENT DOCUMENTS

| | | |
|---|---|---|
| 2,752,060 | 6/1956 | Martin . |
| 2,827,193 | 3/1958 | Martin . |
| 3,166,069 | 1/1965 | Enstrom et al. . |
| 3,399,796 | 9/1968 | Steiner . |
| 4,105,132 | 8/1978 | Keeler . |
| 4,378,015 | 3/1983 | Wardlaw . |
| 4,484,910 | 11/1984 | Sarnoff et al. . |
| 4,620,640 | 11/1986 | Swartzbaugh . |
| 5,085,641 | 2/1992 | Sarnoff et al. . |
| 5,092,843 | 3/1992 | Monroe et al. . |
| 5,102,393 | 4/1992 | Sarnoff et al. . |
| 5,320,609 | 6/1994 | Haber et al. . |
| 5,358,489 | 10/1994 | Wyrick . |
| 5,540,664 | 7/1996 | Wyrick . |
| 5,569,192 | 10/1996 | van der Wal . |

FOREIGN PATENT DOCUMENTS

95/21645    8/1995    (WO) .

*Primary Examiner*—Mark Bockelman
(74) *Attorney, Agent, or Firm*—Pillsbury Madison & Sutro LLP

(57) ABSTRACT

The present invention relates to an automatic injector having a drive assembly with an actuator extending from the rearward end portion of the housing and a removal resistant cover for preventing unintended operation of the actuator. The present invention also relates to a sealing arrangement wherein the needle is sealed within a sterilized needle chamber by at least three sealing members which cooperate to form the chamber. Also, the present invention relates to an injector in which the cartridge is mounted to a tubular cartridge mounting portion of the needle carrier with an annular sealing member disposed therebetween. The cartridge mounting portion has at least one generally axially extending groove which allows air to escape from the cartridge mounting portion as the cartridge is being moved forwardly to a medicament supplying position.

39 Claims, 9 Drawing Sheets

AUTOMATIC INJECTOR

This application claims the benefit of U.S. Provisional Application No. 60/069,775, filed Dec. 16, 1997.

The present invention relates to automatic injectors for delivering medicament to an injection site.

Basically, an automatic injector is a device for enabling an individual to self-administer a dosage of liquid medicament into his or her flesh. The advantage of automatic injectors is that they contain a measured dosage of a liquid medicament in a sealed sterile cartridge and can be utilized for delivering the medicament into the flesh during emergency situations. Another advantage of automatic injectors is that the self-administration of the medicament is accomplished without the user initially seeing the hypodermic needle through which the medicament is delivered and without having the user to manually force the needle into his or her own flesh. Examples of such known injectors are disclosed in U.S. Pat. Nos. 5,085,641, 5,540,664, 5,569,192 and 5,092,843.

One problem with known automatic injectors is that they usually use a flexible rubber sheath to keep the needle sterile. The rubber sheath slides over the forward end of the needle and is sealed to the needle carrier. The needle carrier in turn is sealed to the forward end of the cartridge. Together, the sealing between the cartridge and the needle carrier and the rubber sheath provide sealed chamber which prevents unsterilized air from contaminating the needle. These rubber sheathes are difficult to assemble onto the needles and are susceptible to tearing during manufacturing. Also the cartridge and needle assembly are oftentimes assembled together separately from the housing components. In this situation, the sheath and needle extend forwardly from the cartridge with no structural housing components protecting them. Thus, the needle can pierce sheath if it is dropped or abutted against a solid contact surface. When the sheath is pierced, the needle and interior surfaces of the sheath are no longer sterile and these components must be disposed of.

Thus, there exists a need for an improved way of maintaining the sterility of the needle within the automatic injector so as to prevent unsterilized air from contaminating the needle and the other sterilized surfaces associated therewith. In order to meet this need, the present invention provides an automatic injector comprising a housing having opposed forward and rearward end portions. The forward end portion is engageable with a portion of flesh defining an injection site. A needle assembly comprises a needle carrier with a sterilized interior, a tubular substantially rigid protective needle cover with a sterilized interior, and a sterilized needle mounted within the needle carrier. The needle has a forward tip portion, a rearward tip portion, and a fluid passageway formed therein open to the forward and rearward tip portions. The needle cover has a substantially rigid tubular wall defining a forwardly facing needle passing opening and a rearwardly facing needle carrier receiving opening. The needle carrier and the needle are mounted within the needle carrier receiving opening.

The needle carrier is movable relative to the housing and the protective needle cover between (1) a normal, inoperative position wherein the needle is disposed entirely within the housing and the needle cover and (2) an injecting position wherein the forward tip portion of the needle extends forwardly of the housing through the needle passing opening in the protective needle cover. The needle assembly further comprises a first sealing member substantially sealing the needle passing opening when the needle is in the inoperative position thereof and a second sealing member having an annular shape and being disposed between the needle carrier and the needle cover so as to substantially seal the needle guide receiving opening of the needle cover when the needle is in the inoperative position thereof. A medicament cartridge has a sealed interior containing a supply of fluid medicament.

The needle carrier has a tubular cartridge mounting portion defining a rearwardly facing opening. The cartridge is mounted to the cartridge mounting portion of the needle carrier. The medicament cartridge is normally sealed from the needle. The medicament cartridge and the needle are constructed and arranged to be fluidly communicated during an automatic injecting operation such that the rearward tip portion of the needle pierces the cartridge and extends rearwardly into the cartridge interior so as to fluidly communicate the fluid passageway of the needle with the cartridge interior and allow the fluid medicament contained in the cartridge interior to flow into the fluid passageway.

A third sealing member has an annular shape and is disposed between the tubular cartridge mounting portion of the needle carrier and the cartridge so as to substantially seal the rearwardly facing opening of the cartridge mounting portion when the cartridge is in the inoperative position thereof. The first, second and third sealing members cooperate with the sterilized interior of the needle cover and the sterilized interior of the needle carrier to define a substantially sealed sterilized needle chamber with the needle disposed therein such that unsterilized ambient air is prevented from entering the needle chamber and contaminating either the needle or the chamber.

A manually operable drive assembly has an actuator extending generally rearwardly from the rearward end portion of the housing. The drive assembly is constructed and arranged such that a user can perform the automatic injecting operation by engaging the forward end portion of the housing with the aforesaid injection site and manually operating the actuator such that the drive assembly moves both the needle to the injecting position thereof and causes the cartridge and the needle to be fluidly communicated so that the forward tip portion of the needle pierces the injection site and the rearward tip portion of the needle pierces the cartridge. The drive assembly then subsequently forcing the fluid medicament outwardly from the cartridge interior through the fluid passageway of the needle and into the injection site.

It can thus be appreciated that an automatic injector constructed in accordance with the principles of this aspect of the invention does not require the use of a problematic rubber sheath to keep the needle sterile. Instead, the three sealing members cooperate to maintain the sterility of the needle and the needle chamber. These sealing members are not mounted directly to the needle and thus will not be pierced or unsealed as easily as the sheath. It is to be understood that the needle cover does not have to be of the extendible type which moves forwardly to protect the needle after the injection operation has been performed. Instead, the needle cover could serve to protect the needle only during assembly. However, the extendible needle cover is preferred for safety reasons.

Another aspect of the present invention relates to the provision of a removal resistant cap. In automatic injectors it is desirable to provide a cap which is not easily removable so that the actuator is not accidentally operated. For example, it may desirable to prevent children from accidentally actuating the drive assembly of an injector. Also, it would be undesirable to have the cap unintentionally fall off, thereby exposing the actuator. Current actuator caps or covers are easily removed simply by turning the cap until a set of lugs is aligned with corresponding grooves or openings in the housing rear end. An example of this type of arrangement is disclosed in commonly owned U.S. Pat. No. 5,085,641. The arrangement disclosed in the '641 patent is suitable for applications in which it is desired not to make removal of the cap too difficult. For example, in some applications it is desirable that children and other persons with limited manual dexterity should be able to use the injector in an emergency situation. However, in certain applications it is undesirable that a child should be able to remove the cap and operate the injector. Thus, there exists a need for an automatic injector with an actuator cap or cover having increased removal resistance.

In order to satisfy this need the present invention provides an automatic injector comprising a housing having a longitudinal axis and opposed forward and rearward end portions. The forward end portion is engageable with a portion of flesh defining an injection site. A needle has a forward tip portion, a rearward tip portion, and a fluid passageway formed therein opened to the forward and rearward tip portions. The needle is movable relative to the housing between (1) a normal, inoperative position wherein the needle is disposed entirely within the housing and (2) an injection position wherein the forward tip portion of the needle extends forwardly of the housing forward end portion.

A medicament cartridge has a sealed interior containing a supply of fluid medicament. The medicament cartridge is normally sealed from the needle. The medicament cartridge and the needle are constructed and arranged to be fluidly communicated during an automatic injecting operation such that the rearward tip portion of the needle pierces the cartridge and extends rearwardly into the cartridge interior so as to fluidly communicate the fluid passageway of the needle with the cartridge interior and allow the fluid medicament contained in the cartridge interior to flow into the fluid passageway. A manually operable drive assembly has an actuator extending generally rearwardly from the rearward end portion of the housing. The drive assembly is constructed and arranged such that a user can perform the automatic injecting operation by engaging the forward end portion of the housing with the aforesaid injection site and manually operating the actuator such that the drive assembly moves both the needle to the injecting position thereof and causes the cartridge and the needle to be fluidly communicated so that the forward tip portion of the needle pierces the injection site and the rearward tip portion of the needle pierces the cartridge. The drive assembly then subsequently forcing the fluid medicament outwardly from the cartridge interior through the fluid passageway of the needle and into the injection site.

A removal resistant actuator cover is positioned on the rearward end portion of the housing so as to cover the actuator and prevent unintended operation of the actuator. The cover has an annular wall portion made from yieldingly deformable material. One of the actuator cover and the housing rearward end portion provides a generally radially extending locking projection and the other of the actuator cover and the housing rearward end portion has structure defining a generally radially extending shoulder surface and a generally axially extending groove open to the shoulder surface. The cover and the housing rearward end portion are constructed and arranged such that the cover can be turned relative to the housing rearward end portion about the aforesaid longitudinal axis from (1) a removal resisting position wherein the locking projection and the groove are out of circumferential alignment with respect to one another so that the shoulder surface and the projection cooperate to prevent the cover from being moved axially outwardly relative to the housing rearward portion and (2) a removal allowing position wherein the locking projection and the groove are in substantial circumferential alignment with respect to one another so that the cover can be removed from the housing rearward portion by moving the cover axially outwardly relative to the housing rearward portion so as to expose the actuator and permit manual operation thereof. The one of the cover and the housing rearward end portion has a movement limiting projection substantially circumferentially aligned with the groove. The actuator cover is constructed and arranged such that the user can manually deform the annular wall portion by applying manual pressure thereto so as to affect generally radial relative movement between the locking projection and the movement limiting projection from normal, locking positions to releasing positions. The movement limiting projection is positioned and configured such that, when the locking projection and the movement limiting projection are in the locking positions thereof, the locking projection will engage the movement limiting projection as the cover is being turned toward the removal allowing position thereof to thereby prevent the cover from being turned into the removal allowing position. The movement limiting projection is also positioned and configured such that, when the locking projection and the movement limiting projection are in the releasing positions thereof, the locking projection will pass over the movement limiting projection as the cover is being turned towards the removal allowing position thereof to thereby allow the cover to be turned into the removal allowing position.

Preferably, the locking projection is provided on the interior of the cap and both the movement limiting projection and the structure defining the groove and shoulder surface are provided on the rearward end portion of the housing. However, the components of this preferred structural arrangement could be reversed in practicing the principles of this aspect of the present invention.

Another aspect of the present invention relates to an arrangement wherein pressure is prevented from building tip within the needle carrier as a result of the cartridge moving forwardly to it medicament supplying position. In an arrangement where the cartridge is slidably mounted to a tubular cartridge mounting portion of a needle carrier for relative movement towards the rearward tip portion of the needle, a sealing member can be disposed between the cartridge and the cartridge mounting portion to provide sealing. If this seal remains intact as the cartridge moves forwardly towards its medicament supplying position, pressure can build up inside the needle carrier. This pressure build-up can interfere with proper injection of the medicament as a result of the air being forced into the cartridge and outwardly through the needle into the injection site or as a result of the pressure providing resistance to forward cartridge movement.

Therefore, it is another object of the present invention to provide an automatic injector in which such pressure build-up is prevented. In order to achieve this object. another aspect of the present invention provides an automatic injector comprising a housing having opposed forward and rearward end portions. The forward end portion is engageable with a portion of flesh defining an injection site. A needle assembly comprises a needle carrier with a sterilized interior. and a sterilized needle mounted within the needle carrier. The needle having a forward tip portion, a rearward tip portion, and a fluid passageway open to both the forward and rearward tip portions. The needle carrier is movable relative to the housing between (1) a normal, inoperative position wherein the needle is disposed entirely within the housing and (2) an injecting position wherein the forward tip portion of the needle extends forwardly of the housing through the opening in the housing forward end portion.

The needle assembly comprises sealing structure substantially sealing a forward portion of the needle carrier and the forward tip portion of the needle. The sealing structure according to this aspect of the invention may be considered to encompass the sheathed conventionally used to seal the forward tip portion of the needle. However, it is preferred to use the sealing arrangement discussed above in view of the problems associated with sheaths.

A medicament cartridge has a sealed interior containing a supply of fluid medicament. The needle carrier has a tubular cartridge mounting portion defining a rearwardly facing opening. The cartridge is slidably mounted to the cartridge mounting portion of the needle carrier. The medicament cartridge is movable relative to the needle between (1) a normal, inoperative position wherein the cartridge is unpierced and disposed rearwardly of the rearward tip portion of the needle and (2) a medicament supplying position wherein the cartridge is moved forwardly of the inoperative position thereof such that the rearward tip portion of the needle pierces the cartridge and extends rearwardly into the cartridge interior so as to fluidly communicate the fluid passageway of the needle with the cartridge interior and allow the fluid medicament contained in the cartridge interior to flow into the fluid passageway.

An annular sealing member is disposed between the cartridge and the cartridge mounting portion of needle carrier so as to substantially seal the rearwardly facing opening of the cartridge mounting portion when the cartridge is in the inoperative position thereof. The sealing structure and the sealing member cooperate with the sterilized interior of the needle carrier to define a substantially sealed sterilized needle chamber with the needle disposed therein such that unsterilized ambient air is prevented from entering the needle chamber and contaminating either the needle or the chamber when the needle carrier and the cartridge are in the inoperative positions thereof. The tubular cartridge mounting portion has at least one generally axially extending groove formed thereon. The groove being positioned and configured to allow air to escape from the sterilized interior of the cartridge mounting portion as the cartridge is being moved forwardly to the medicament supplying position thereof to thereby prevent a pressure build-up in the cartridge mounting portion.

A manually operable drive assembly has an actuator extending generally rearwardly from the rearward end portion of the housing. The drive assembly being constructed and arranged such that a user can perform an automatic injecting operation by engaging the forward end portion of the housing with the aforesaid injection site and thereafter manually operating the actuator such that the drive assembly moves both the needle carrier to the injecting position thereof and the cartridge to the medicament supplying position thereof so that the forward tip portion of the needle pierces the injection site and the rearward tip portion of the needle pierces the cartridge and then the drive assembly forces the fluid medicament outwardly from the cartridge interior through the fluid passageway of the needle and into the injection site.

Yet another aspect of the present invention relates to the actuator which facilitates operation of the drive assembly. In the '641 patent mentioned above, an actuating pin extends rearwardly from the rear end of the housing. The pin has a circular head with a relatively thin axial thickness and a thin intermediate section extending forwardly therefrom. This construction is relatively weak and can allow the thin intermediate section to bend during actuation if pressure is not applied directly in forward direction. Accordingly, it is a further object of the present invention to provide a more robust actuator which is less prone to such bending. In order to achieve this object, the present invention provides an automatic injector comprising a housing have opposed forward and rearward end portions. The forward end portion is engageable with a portion of flesh defining an injection site. A needle has a forward tip portion, a rearward tip portion, and a fluid passageway formed therein open to the forward and rearward tip portions. The needle is movable relative to the housing between (1) a normal, inoperative position wherein the needle is disposed entirely within the housing and (2) an injecting position wherein the forward tip portion of the needle extends forwardly of the housing through the opening in the forward end portion.

A medicament cartridge has a sealed interior containing a supply of fluid medicament. The medicament cartridge is normally sealed from the needle. The medicament cartridge and the needle are constructed and arranged to be fluidly communicated during an automatic injecting operation such that the rearward tip portion of the needle pierces the cartridge and extends rearwardly into the cartridge interior so as to fluidly communicate the fluid passageway of the needle with the cartridge interior and allow the fluid medicament contained in the cartridge interior to flow into the fluid passageway.

A manually operable drive assembly has an actuator extending generally rearwardly from the rearward end portion of the housing. The drive assembly is constructed and arranged such that a user can perform the automatic injecting operation by engaging the forward end portion of the housing with the aforesaid injection site and manually operating the actuator such that the drive assembly moves both the needle to the injecting position thereof and causes the cartridge and the needle to be fluidly communicated so that the forward tip portion of the needle pierces the injection site and the rearward tip portion of the needle pierces the cartridge. The drive assembly then subsequently forcing the fluid medicament outwardly from the cartridge interior through the fluid passageway of the needle and into the injection site. The actuator has a head with an exterior side wall surface and the housing rearward end portion has a interior surface defining an actuator head receiving opening. The exterior side wall surface and the interior surface of the housing rearward end portion are positioned and configured such that a portion of the actuator head is received within the actuator head receiving opening with the exterior side wall surface of the actuator head facing the interior surface of the housing rearward end portion in closely spaced relation so as to substantially prevent radial bending of the actuator before manual operation thereof. It is to be understood that the principles of this aspect of the invention are not limited in the disclosed embodiment and may be practiced with any automatic injectors now known or later developed.

Other objects, advantages, and features of the present invention will become apparent from the following detailed description, the accompanying drawings, and the appended claims.

DETAILED DESCRIPTION OF THE INVENTION

Figure 1:
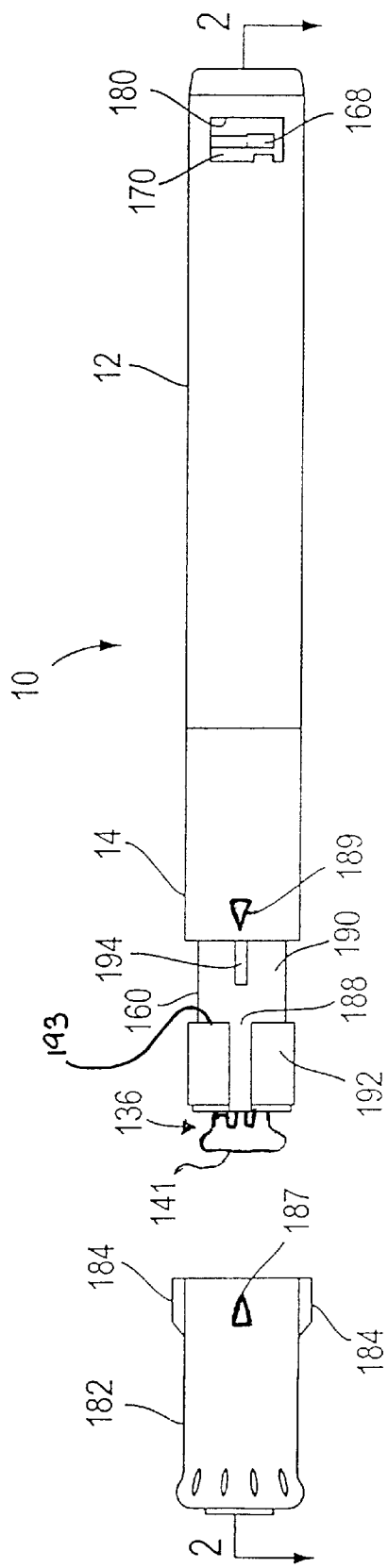
FIG. 1 is an elevated view of an automatic injector having removal resistant cover constructed in accordance with the principles of the present invention.

FIG. 1 shows an auto injector, generally indicated at 10, constructed in accordance with principles of the present invention. The auto-injector 10 is generally comprised of a forward housing member 12 and a rearward housing member 14 connected together to define a housing with a longitudinal axis. A removal resistant cap 182 can be removed from the rear housing member to gain access to an actuating pin 136 that allows the user to initiate an automatic injection of an encapsulated medicament as will be described.

Figure 2:
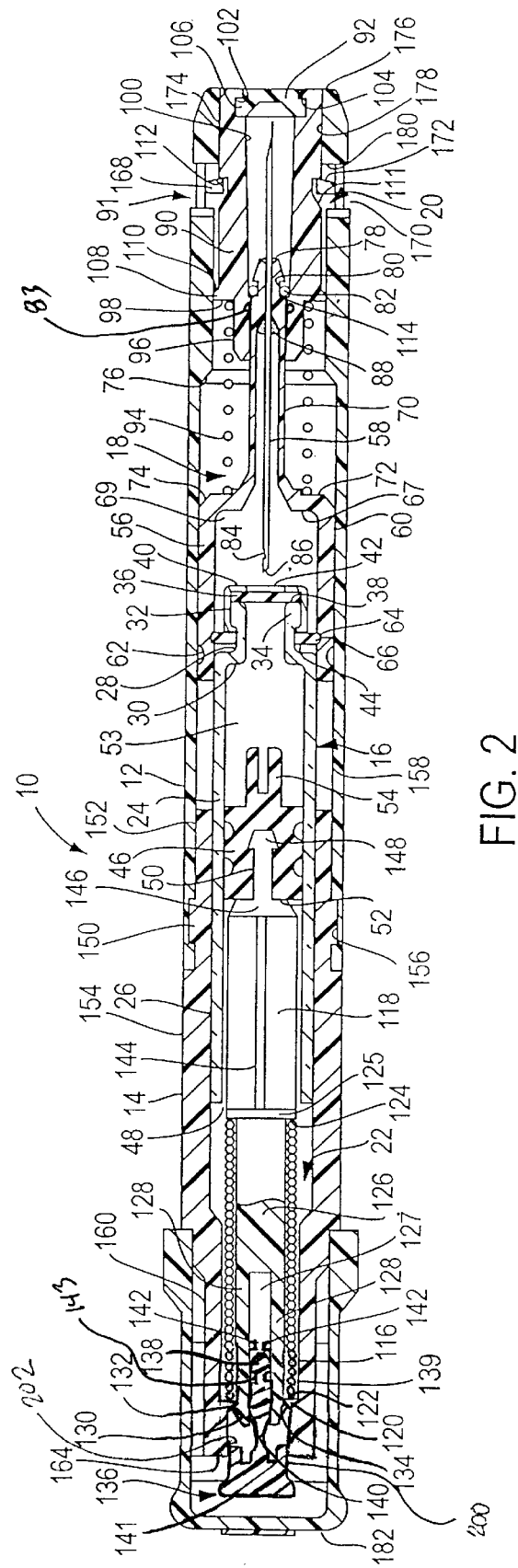
FIG. 2 is a longitudinal sectional view in partial elevation along line 2—2 of FIG. 1 of the auto-injector assembled and constructed in accordance with the principles of the present invention.

As shown in FIG. 2, the forward housing member 12 is an elongated, generally tubular, cylindrical plastic member that contains a dental cartridge assembly, generally indicated at 16, and a needle assembly, generally indicated at 18 and including a protective needle cover assembly 20. The rearward housing member 14 is an elongated, generally tubular cylindrical plastic member containing a manually operable drive assembly, generally indicated at 22. The rearward housing member 14 is removably fixed to the forward housing member 12 by a snap-fit connection, as will be described herein.

The dental cartridge assembly 16 includes a medicament container in the form of a dental cartridge 24, which is tubular and made of glass. The dental cartridge 24 has forwardly and rearwardly facing openings at its opposite ends and is necked down at its forward end. More particularly, a major rearward portion 26 of the cartridge 24 extends rearwardly of a forward portion 28 and has an inner diameter which is larger than the inner diameter of the necked down forward portion 28. The dental cartridge 24 has an inwardly extending annular shoulder 30 which integrally connects the main rearward portion 26 with the smaller diameter forward portion 28. A forwardmost end 32 of the dental cartridge 24 has a radially extending annular flange 34 which receives a generally circular cartridge sealing member 36, preferably made of an elastic or rubber material. The sealing member 36 is peripherally secured to an annular outer surface 38 of the flange 34 at the forward end 32 of the cartridge 24 by means of an annular metallic clamping ring 40, thereby sealing off the forwardly facing opening at the forwardmost end 32 of the cartridge 24. The clamping ring 40 has a centrally disposed aperture 42 to enable the sealing member 36 to be pierced by a rearward tip portion of a needle 58 of the needle assembly 18 upon actuation of the drive assembly 22.

The necked-down portion 28 of the cartridge 24 has a rubber washer 44 fixedly mounted thereto in surrounding relation. The washer 44 may be referred to as a third sealing member whose sealing function will be discussed below. A movable plunger 46, also preferably made of an elastic or rubber material, closes and internally seals the open rearward end 48 of the dental cartridge 24 and has a small, centrally disposed bore 50 in its rear face 52. The bore 50 provides a means for directly connecting to the drive assembly 22. The movable plunger 46 and sealing member 36 cooperate to seal a medicament 53 within the cartridge 24. Preferably, the plunger 46 has a forwardly extending nipple type configuration 54 constructed and arranged to fit within the smaller inner diameter of the forward end of the cartridge 24 so as to substantially expel all medicament from the cartridge 24. The plunger 46 is slidably mounted within cartridge 24 for forward sliding movement in sealing relation with the interior surface of the cartridge 24. The aforementioned arrangement for the nipple type plunger 46 and the dental cartridge 24 are disclosed in the U.S. patent application Ser. No. 08/280,884 (abandoned in favor of a continuation application, U.S. patent application Ser. No. 08/548,762, issued as U.S. Pat. No. 5,713,866), which is incorporated by reference into the present application. It can be appreciated, however, that this arrangement is merely preferred and that the present invention contemplates that any type of plunger now known or later developed can be used.

The needle assembly 18 comprises a needle carrier 56 and a sterilized hypodermic needle 58 mounted to the carrier 56. The needle carrier 56 has a substantially cup-shaped or tubular cartridge mounting portion 60 having a rearwardly facing cartridge receiving opening. The forward end 28 of the medicament cartridge 24 extends partially into the cartridge mounting portion 60 in telescopic relation. An annular groove 62 is formed externally at the rear of the cup-shaped portion 60. The interior surface of cartridge mounting portion 60 towards the rear thereof has an annular detent groove 64. A peripheral edge 66 of rubber washer 44 engages the detent groove 64, preventing forward movement of the medicament cartridge 24 relative to the needle assembly 18 prior to or during the initial phase of injector activation.

Figure 10:
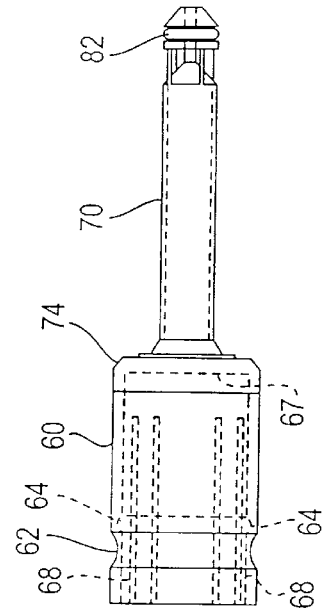
FIG. 10 is an enlarged side plan view of the needle carrier showing the longitudinal, internal slots in dashed lines.

As can best be seen in FIG. 10, the internal surface of the cartridge mounting portion 60 of the needle assembly 18 has a series of circumferentially spaced, narrow, longitudinal slots or grooves 68 starting from the rearwardmost end of the mounting portion 60 and extending forwardly toward the rearwardly facing annular surface 67, thus traversing the detent groove 64. Because the groove 64 is of the same or greater depth relative to the depth of slots 68, the annular elastic washer 44 forms an airtight seal with groove 64. However, when the cartridge 24 and washer 44 are moved forwardly relative to needle assembly 18 to a medicament supplying position, the slots 68 forwardly of groove 64 allow bleeding/venting of the air within space 69 of mounting portion 60 past the washer 44 in order to prevent any pressure build-up in space 69 which might hinder medicament injection or otherwise cause air to be forced into the cartridge 24 and out through the needle 58. The slots 68 rearwardly of groove 64 also prevent pressure build-up in space 69 during assembly.

Although the disclosed medicament cartridge is movable, it is to be understood that some aspects of the present invention may be practiced without the use of movable cartridge. For example, the type of cartridge wherein the forward seal bulges out to be pierced by the needle as a result of pressure applied by the drive assembly may be used.

Referring back to FIG. 2, the needle carrier 56 has a substantially narrowed diameter tubular forward portion 70 disposed in surrounding relation to the hypodermic needle 58, thus forming a forwardly facing annular engaging surface 72 at the transition between mounting portion 60 and forward portion 70. The flange surface 72 is chamfered along an outer peripheral sloped edge 74 to allow for smooth forward sliding motion within the forward housing member 12. Upon activation of the device, forward movement of needle assembly 18 causes edge 74 to eventually engage a rearwardly facing engaging surface 76 formed internally on the forward housing member 12. A forwardmost portion 78 of tubular portion 70 has an "O" ring groove in which an O-ring 82 is placed in sealing relation to an interior surface 100 of the protective needle cover 20. The O-ring 82 may be referred to as a second sealing member whose sealing function will be discussed below. The O-ring 82 may either seal the path hermetically or define a tortious path around it through which the air will not flow under normal conditions.

The interior of the needle cover 90 has an annular groove 83 formed thereon. This groove 83 receives the O-ring 82 before the cover 90 and carrier 56 are assembled with the housing. The groove 83 and the O-ring 82 cooperate to keep the cover 90 locked in place. When the unit is assembled, the cover 90 is pushed rearwardly so that the groove 83 disengages from the O-ring 82 with the O-ring being disposed in the location shown in FIG. 2.

The hypodermic needle 58 is a substantially narrow, elongated hollow tubular steel member with forward and rearward tip portions. Preferably, the needle 58 has a lateral slot 84 on one side thereof at the rearward tip portion 86 to allow unimpeded flow of fluid through the needle, even in the event of an obstruction at the rearward opening at rearward end 86 of the needle 58. The forward tip portion also has an opening to allow the medicament to flow into the injection site. The openings in the forward tip portion and the rearward tip portion are communicated by a fluid passageway. The type of needle shown is known as an 'anti-coring needle', an example of which is disclosed in U.S. Pat. No. 5,716,348. It is to be understood that the location of the openings on the needle are not critical and may be located at the very tip of each end or spaced inwardly therefrom along the tip portions. The rearward tip portion 86 of the needle 58 is configured to puncture the medicament cartridge sealing member 36 to establish fluid communication with medicament 53. The needle 58 is secured at a central exterior portion thereof to needle carrier 56 of the hub assembly 18 by means of an adhesive 88 or any other suitable means.

As shown in FIG. 2, the protective needle cover assembly, indicated at 20 comprises a rigid plastic protective cover 90 and a forwardly disposed rubber seal 92 at the forward end of cover 90 providing a sterile barrier for the needle 58, a cover locking assembly 91, and a cover extension spring 94. The seal 92 may be referred to as a first sealing member whose sealing function will be discussed below. The protective cover 90 is substantially tubular, and has a rearward portion 96 of a slightly smaller outer diameter so as to form a rearwardly facing annular shoulder 98. The spring 94 has its forward volute resting on the rearwardly facing annular shoulder 98 and its rearward volute resting on the forwardly facing annular engaging surface 72 formed on the needle carrier 56 with the spring 94 slightly stressed therebetween. The inner surface 100 of the needle cover 90 tapers outwardly as it extends forwardly, thus enabling disengagement of O-ring 82 with surface 100 during activation and providing for unimpeded movement of the needle carrier 56 and needle 58 through needle cover 90. The protective cover 90 is biased by the extension spring 94 to move forwardly in surrounding protective relation over the needle 58 after actuation of the injection device 10 as will be described.

The inner surface of the forward end of the protective needle cover 90 has an inwardly facing annular groove 102 forming an annular shoulder 104 at the forwardmost end. The rubber seal 92 is securely fixed into groove 102 an outwardly extending peripheral edge 106 of the seal 92 received in groove 104. A radially projecting annular ridge 108 is formed on the exterior of the protective cover 90 and has a rearwardly and outwardly sloping surface 110. Mid-positioned on the protective cover 90 is a radially inwardly and forwardly tapering surface portion 111 forwardly terminating in an annular groove, and a rearwardly facing annular shoulder 112. Formed on the interior surface 100 of the protective cover 90 is an inwardly extending 114 protrusion that acts as a backstop for O-ring 82.

Upon assembly of the injection device 10, and as can best be seen in FIG. 2, the forward tip portion of needle 58 and the forward portion 70 of the needle carrier 56 are telescopically received into the carrier receiving opening of the needle cover 90, with the spring 94 mounted between the needle carrier 56 and cover assembly 20. The O-ring 82 is pushed over the protrusion 114 and, once in position, the cover 90 and needle carrier 56 cannot be easily pulled apart. With the spring 94 slightly tensioned, the O-ring 82 backseats against the protrusion 114 and, acting in cooperation with the protective cover forward seal 92, seals the forward tip portion of the needle 58 within the cover 90. With the medicament cartridge washer 44 engaged with the needle hub detent groove 64 so as to seal the rearward tip portion of the needle 58 within space 69, the entire needle 58 is sealed airtight after assembly. As a result, the medicament 53 can be sterilized, e.g., by steam autoclaving after assembly, without exposing the needle 58 to moisture or other elements during sterilization. Preferably, however, these components are sterilized before assembly and then assembled in a sterile area. Also, the sealing maintains the sterility of the needle 56 by preventing contaminated (i.e., non-sterile) air from entering the needle assembly 18 and thereby contaminating the needle 58. Another way to state the sealing function is that first sealing member (seal 92), the second sealing member (O-ring 82), and the third sealing member (washer 44) cooperate with the sterilized interior of the needle cover 90 and the sterilized interior of the needle carrier 56 to define a substantially sealed sterilized needle chamber with the sterilized needle 58 disposed therein such that unsterilized ambient air is prevented from entering the chamber and contaminating either the chamber or the needle 58. The type, configuration, or positioning of the sealing members can be changed or modified as long as such substantial sealing is provided. The sealing may be hermetic or via tortious paths formed around the seals.

Preferably, the needle carrier 56 is mounted to the needle cover 90 and the cartridge 24 is mounted to the needle carrier 56 in a sterilized area, such as a sterile room. The needle 58 may be pre-mounted to the needle carrier 56 or may also be mounted to the needle carrier in a sterile area. After assembly these components define a needle and guide cartridge assembly which may be carried or shipped to an unsterile assembly area where the drive assembly 22 and the needle and guide assembly can be mounted within the housing. The use of the needle cover 90 is particularly useful in this assembly method because the cover 90 provides rigid protection for the needle 58.

As shown in FIG. 2 releasable spring drive assembly 22 is provided within the rearward housing portion 14 of the injector device 10. The drive assembly 22 includes a coil drive spring 116 and a molded plastic collet member, generally indicated at 118. The rearward housing member 14 is formed with an interior annular flange 120 spaced forward of the rearwardmost end thereof. The forward surface 122 of the annular flange 120 is adapted to be engaged by a rearward volute of the drive spring 116, which operates as a releasable energy source for the injector 10 of the present invention. The forward volute of the drive spring 116 engages a rearwardly facing surface 124 of a mid-positioned flange 125 of the collet member 118.

The collet member 118 further includes a longitudinal, cylindrical shaft portion 126 that extends rearwardly from the mid-positioned flange 125 within the interior of drive spring 116. A rearward end portion of the cylindrical shaft portion 126 is split so as to form a plurality (two) of rearwardly extending, resilient collet arms 128 separated by a space 127. The rearward peripheral portion of the arms 128 are formed with radially outwardly extending flanges 130 presenting forwardly facing locking surfaces 132 which are adapted to engage along annular surface 134 of the interior annular flange 120 of the rear housing member 14.

An actuator in the form of an actuating pin member 136 is disposed between the resilient arms 128, locking them apart in a storage or inoperative position. More specifically, pin 136 comprises a forward portion 138 that extends into the slot 127 between the resilient arms 128, preventing arms 128 from moving towards one another in FIG. 2. The actuating pin member 136 also has an intermediate portion 140 of a reduced diameter with respect to the forward portion 138, there being a frustoconical transition between the two portions. A rigid, generally cylindrical head 141 is formed at the back end of the intermediate portion 140. The head 141 has a generally cylindrical side wall surface 200 with an exterior diameter slightly smaller than the interior surface 202 of the rearward end portion of the rearward housing portion 14.

The interior surface 202 of the rearward end portion defines an actuator head receiving opening and a portion of the actuator head 141 is received therein such that the exterior side wall surface 200 thereof faces the interior surface 202 in closely spaced relation. This closely spaced relation substantially prevents radial bending of the pin member 136 and provides a more robust actuator. Thus, damage to the pin member 136 can be prevented to ensure proper actuation of the drive assembly 22. Also, the head 141 is solid and has two grooves 204 extending laterally thereacross. It is to be understood that the head 141 have other configurations other than cylindrical. For example, it is contemplated that the head 141 could have a square cross-section.

The larger forward portion 138 of pin member 136 is cylindrically formed and, in the assembled position shown, engages the rearward, generally arcuate inner facing surfaces 139 of the resilient arms 128 so as to prevent the arms 128 from moving radially inwardly toward one another, thereby maintaining the locking surfaces 132 of the arms 128 in engagement with the rearward facing locking surface 134 of interior flange 120. Thus, the drive spring 116 is retained in stressed position between the mid-positioned flange face 124 of the collet member 118 and the forwardly facing surface 122 of the interior flange 120 of the rearward housing member 14. Radially inwardly extending ridges 142 extend along the inner arcuate surfaces of the collet arms 128. It can be understood that the ridges 142 act as a stop, or detent force, against any applied forward motion of the actuating pin 136 so as to prevent the accidental actuation of the injector device 10 until a sufficient amount of force is applied to clear the ridges 142. When the forward portion 138 first rides over ridges 142, it tends to bias the arms 128 outwardly away from one another. After the majority of forward portion 138 is beyond ridges 142, the arms are forced to collapse inwardly under the force of spring 116 to release surfaces 132 from surface 134, enabling collet 118 to be thrust forward.

An annular groove 143 is formed around the forward portion 138. The groove 143 receives the ridges 142 during forward movement of the pin member 136. This arrangement allows the collapsing of the collet arms to occur sooner and with less force being applied to the pin member 136 in comparison to pin members without such a groove.

A concentric series of elongated guide ribs 144 extend forwardly from the mid-positioned flange 125 to a tapered forward flange 146 and are received into the open rearward end 48 of the medicament cartridge 24. A short, blunt-nosed, substantially arrow shaped portion 148 of reduced diameter extends forwardly from the tapered flange 146 and is received into the centrally located bore 50 at the rear of the plunger 46, thus directly connecting the spring drive assembly 22 to the medicament cartridge plunger 46.

As can be seen in FIG. 2, the forward end of the rearward housing member 14 is telescopically received into the rearward end of the forward housing member 12. More particularly, the forward end of the rearward housing member 14 has an annular flange 150 radially extending outwardly from an exterior surface 152 thereof. The exterior surface 152 is of a narrower outer diameter than that of the main body of the rearward housing member 14 so as to permit the telescopic reception. The forward housing member 12 has an annular groove 156 formed on the interior surface 158 toward the rearward portion thereof. The forward housing member 12 is secured to the rear housing member 14 by rearwardly sliding the rearward end of the forward housing member 12 in telescoping relation over the forward end of the rear housing member 14 until the annular flange 150 of the rear housing member 14 snaps into the annular groove 156 of the forward housing member 12.

A rearward end portion 160 of the rearward housing member 14 has an outer diameter that is smaller than the main central portion 154 and sized to receive the removal resistant cover 182. As best seen in FIG. 1, the rearward end portion 160 has a forward portion 190 and a rearward portion 192, with the rearward portion 192 having a large outer diameter than forward portion 190. A pair of generally axially extending grooves 188 are formed through rearward portion 192 and form a continuous surface with forward portion 190. A generally radially extending shoulder surface 193 is defined between the forward and rearward portions 190, 192.

As shown in FIGS. 1–6, the forward end of the plastic forward housing member 12 has two integrally formed opposing resilient finger snaps 168 biased radially inward into the housing member 12 through associated openings 170 of the forward housing member 12. The snaps 168 provide forwardly facing locking surfaces 172. The finger snaps 168 are disposed adjacent to and forwardly of the forwardly and radially inwardly tapered surface 111 on the exterior surface of the needle cover 90, and rearwardly of the rearwardly facing needle cover annular shoulder 112. When the injector device 10 is in an assembled storage condition, as shown in FIG. 2, the needle cover 90 is retained within the forward housing member 12 by virtue of the engagement of finger snaps 168 within the groove in the exterior surface of needle cover 90 formed between surfaces 111 and 112.

When the needle cover 90 is automatically deployed after an injection operation, the tapered surface 111 rides past linger snaps 168, forcing finger snaps 168 outwards. Eventually, annular ridge 108 slides past the finger snap locking surfaces 172. Forward movement of the needle cover 90 is stopped when the sloping surface 110 of ridge 108 rides past finger snaps 168 and contacts the rear facing edges 180 formed at openings 170 as shown. When needle cover 90 reaches this position, the snap fingers 168 are disposed such that forwardly facing locking surfaces 172 thereof are behind the needle cover rearwardly facing shoulder 98. Thus, the finger snaps 168 and the shoulder 98 cooperate to secure the needle cover 90 in an extended, needle covering protective position (see FIG. 6) after an injection operation and preventing anyone from pushing the needle cover 90 back into the forward housing member 12 and exposing the needle 58.

Figure 9:
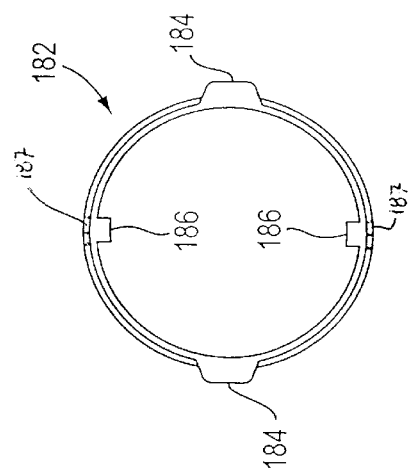
FIG. 9 is an enlarged front end plan view of the cover showing the internal locking projections and external cap releasing portions.
Figure 7A:
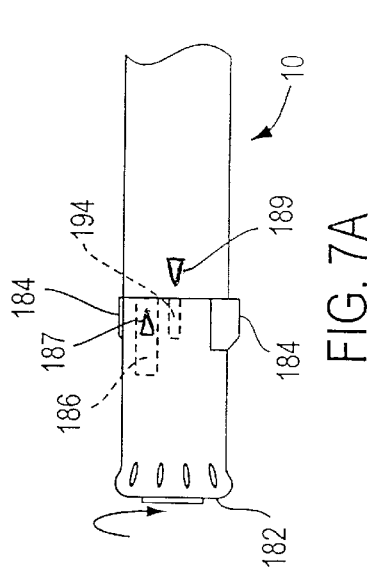
FIG. 7A is a side plan view of the rearward portion of the auto-injector of the present invention and showing the cover being rotated into a position wherein the internal stops in the cap have reached the external stops on the injector body.
Figure 7B:
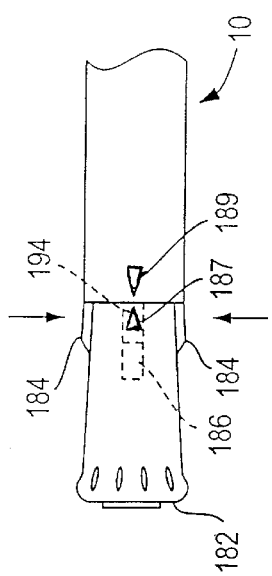
FIG. 7B is a side plan view similar to FIG. 7A showing the removal resistant cover release portions having been squeezed and the subsequent alignment of the indicator arrows by further slight rotation of the cap over the stops.
Figure 7C:
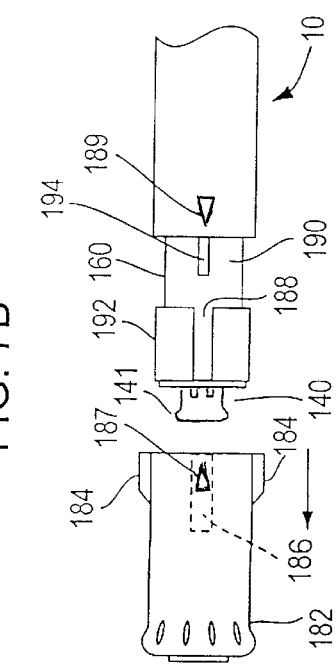
FIG. 7C is a side plan view similar to FIG. 7A showing the removal of the cover from the injector housing, thus exposing the actuator.

As shown in FIGS. 7A, 7B, and 7C, the rearward end portion 160 of the injection device 10 has a generally tubular, molded plastic cover 182 disposed in releasably locked covering relation with respect to actuating pin 136. The cover 182 has an annular side wall portion and a top wall portion formed integrally with the side wall portion. As best seen in FIG. 9, which is a front end plan view of cover 182, the forwardmost end of the cover 182 has two integrally formed, diametrically opposed, outwardly protruding cap release portions 184 on the outer surface. The forwardmost end of cover 182 also has two diametrically opposed, radially inwardly protruding locking projections 186 on the inner surface thereof. The locking projections 186 extend rearwardly from the forwardmost end of the inner surface of the cover 182 to an intermediate portion on the inner surface of the cover 182, as can be appreciated from FIGS. 7A–7C. The inwardly protruding locking projections 186 and the outwardly protruding cap release portions 184 are offset approximately 90 degrees from one another on the forwardmost portion of the cover 182. Alignment indicators 187 are embossed on the outer surface of the cover 182 at positions on the cap corresponding to the positions at which the internal locking projections 186 are disposed. Other alignment indicators 189 are embossed on the rear housing portion 14 at positions longitudinally aligned with the pair of axially extending grooves 188 in the enlarged diameter portion 192. Preferably, the alignment indicators 187, 189 are in the form of arrows as shown, but may be dots or any other recessed, embossed, or labeled indication marking.

As stated previously, the rearward end portion 160 is comprised of a forward portion 190 and a rearward portion 192 with a generally radially extending shoulder surface 193 extending therebetween. The difference in diameter is substantially equal to the height of the locking projections 186 on cap 182.

Figure 5:
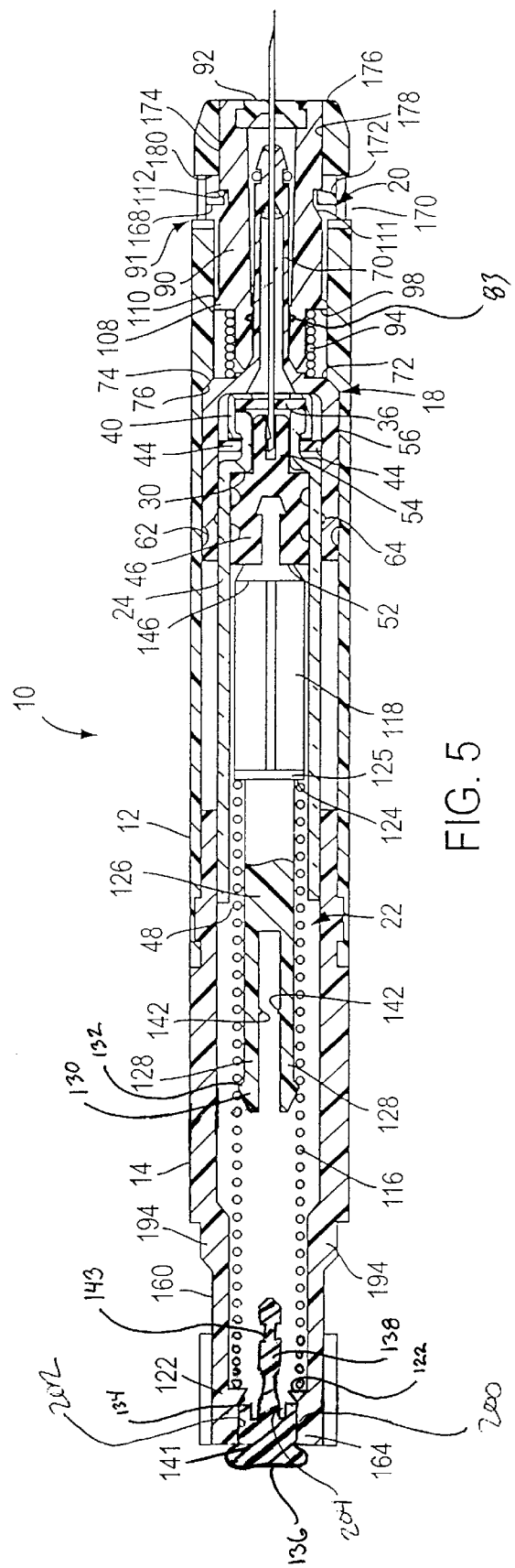
FIG. 5 is a longitudinal view of the auto-injector of the present invention and illustrating the dental cartridge plunger having been moved forward within the cartridge.
Figure 8:
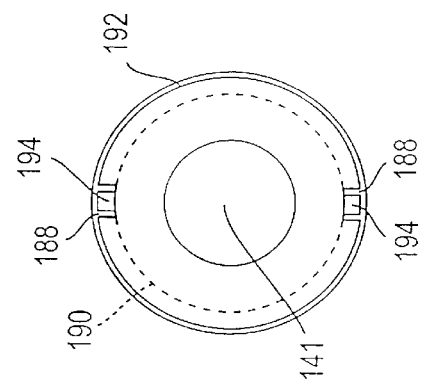
FIG. 8 is an enlarged rear end plan view of the auto-injector device with the cover removed.

As best shown in FIGS. 5, 7C, and 8, two diametrically disposed movement limiting projections 194 are disposed on the forward portion 190. Projections 194 are forwardly disposed from and in general, circumferential alignment with grooves 188 as shown. The projections 194 are also generally circumferentially aligned with indicators 189 and protrude from the rearward end portion 160 generally to the same extent as the locking projections 186 extend inwardly from the inner surface of the cover 182. As can be appreciated in FIG. 7A, the movement limiting projections 194 and the projections 186 abut one another to prevent the alignment indicators 187 and 189 from being aligned with one another upon simple turning of the cover 182. As a result, locking projections 186 cannot be aligned with grooves 188 on the injector body and the cover 182 cannot be removed from covering relation with respect to actuating pin member 136. This position may be considered to be a removal resisting position.

In order to remove the cover 182, the indicators 187 and 189 must be aligned, so that the locking projections 186 of cover 182 can be generally circumferentially aligned with grooves 188 and pulled axially rearwardly therethrough. The cover 182 may be considered to be in a removal allowing position when the locking projections 186 are aligned with the grooves 188. In order to align indicators 187 and 189, the cap release portions 184 must be manually squeezed. The plastic material forming cover 182 is sufficiently yieldingly deformable such that squeezing the portions 184 will distort the cross sectional shape of the cap 182 into a generally oval configuration, thus moving locking projections 186 generally radially outwardly away from one another from a normal, locking position to a releasing position. In this condition, the cover 182 can be rotated so that projections 186 are disposed in overlapping alignment with movement limiting projections 194, as can be appreciated from FIG. 7B. The indicators 187 and 189 are now aligned, and the cover 182 can be pulled off the injection body, with locking projections 186 passing through grooves 188.

It should be noted that the locking projections 186, the grooves 188, the movement limiting projections 194, and the shoulder surface 193 may be reversed so that the structure defining the groove 188 and the shoulder surface 193 is located on the interior of the cap 182 and the locking projections 186 are located on the housing 12. However, the construction shown in the Figures is preferred because it is easier to manufacture.

Figure 3:
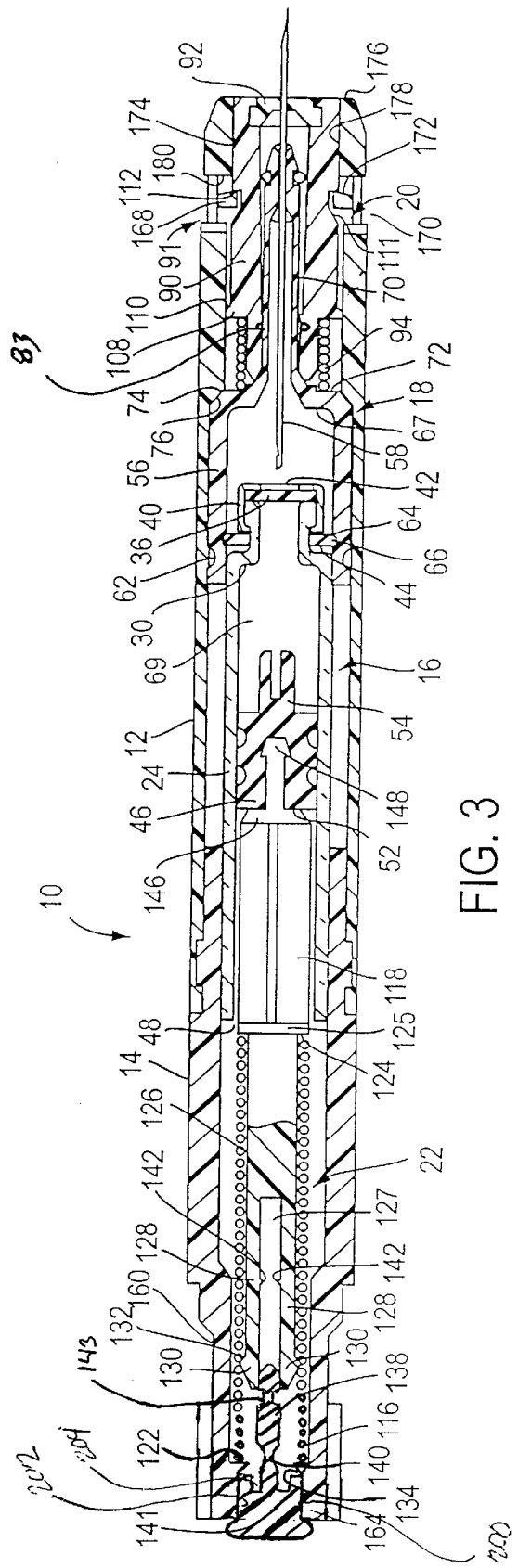
FIG. 3 is a longitudinal sectional view of the auto-injector of the present invention and illustrating the actuation of the drive assembly and subsequent projection of the needle from the front end of the injector after manual depression of the actuator.

As the next step in operating injection device 10, referring to FIG. 3, the user grasps the body of the injector device 10 and places the forwardmost end portion 176 against the portion of flesh to be injected. The actuating pin member 136 is then urged forwardly by a thumb or finger with enough force to overcome the engagement of the forward portion 138 with the ridges 142. The intermediate narrower portion 140 of actuating pin 136 then moves into the slotted area 127, closer to locking surface 132 and 134. The rearward end of the collet arms 128 are thus permitted to deflect inwardly towards the narrower portion 140 to an extent sufficient that the locking surfaces 132 slidingly disengage from the interior annular flange locking surfaces 134 under the force of spring 116. The collet member 118 then moves forwardly by the action of the drive spring 116, initially pulling the pin 136 forward within slot 127. As the collet member 118 continues to move forwardly, the actuating pin member 136 is left behind in captured relation within the cup-shaped end 164 of rear housing member 14 thereby preventing the actuating pin 136 from becoming a loose part.

As shown in FIG. 3, the collet member 118 is driven forwardly against the rear end 52 of the slidable plunger 46. This, in turn, urges both the medicament cartridge 24 and needle carrier 56 forwardly until the peripheral sloped edge 74 of needle carrier 56 engages the engaging surface 76 on the interior surface of forward housing 12, preventing any further forward movement of the needle carrier 56. At this point, the needle 58 is in the injecting position. During this movement, the plunger 46 does not move relative to cartridge 24 due to incompressibility of medicament 53. Also, cartridge 24 does not move relative to needle carrier 56 as a result of the interengagement between the washer 44 and the groove 64. At the same time, the forward movement of the needle carrier 56 compresses the extension spring 94 against the rearwardly facing shoulder 98 of the needle cover 90. Also, the movement of the needle assembly 18 causes the front end of the needle 58 to puncture the rubber seal 92 at the forwardmost end 176 of the injector device 10 and be pushed into the injection site.

Figure 4:
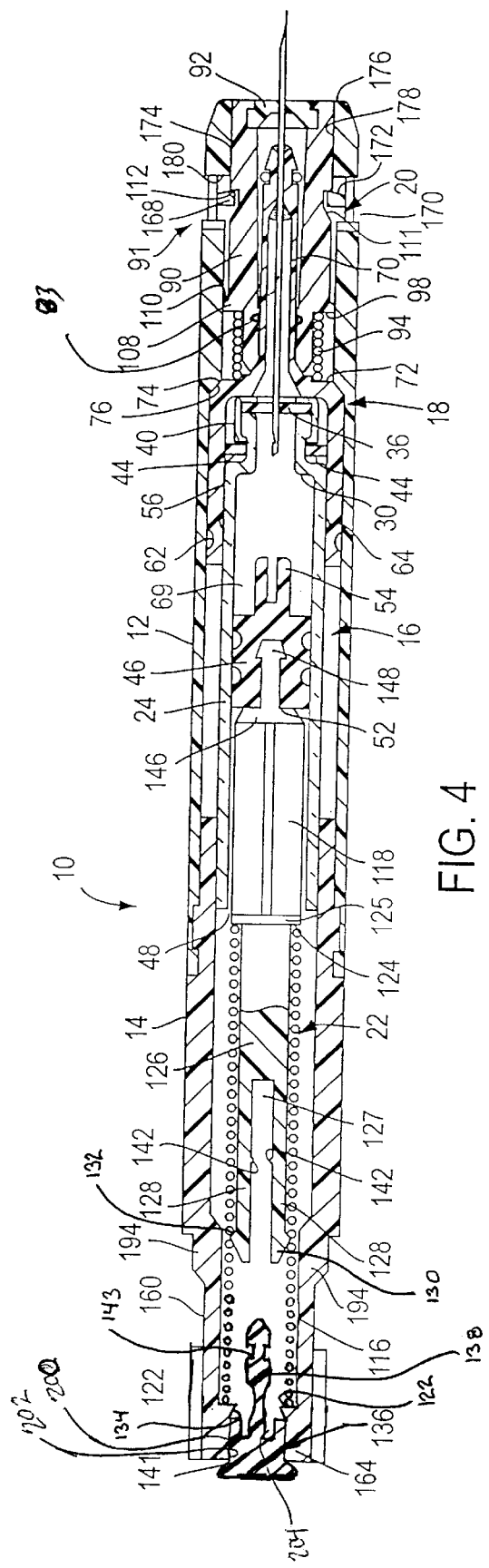
FIG. 4 is a longitudinal sectional view of the auto-injector of the present invention and illustrating the dental cartridge having been moved onto the rear end of the hypodermic needle thereby puncturing the cartridge seal and establishing a flowpath for the fluid medicament.

As can be seen in FIG. 4, when movement of needle carrier 56 stops, the impact load of the engagement between surfaces 74 and 76 forces the washer 44 out of the detent groove 64. The forward end of the cartridge 24 is forced onto the rear tip portion 86 of the needle 58, which pierces the cartridge sealing member 36. Forward movement of the medicament cartridge 24 continues until the front end thereof contacts the rearward facing engaging surface 67 of needle carrier 56. At this point, the cartridge 24 has reached its medicament supplying position.

As is shown in FIG. 5, with the cartridge sealing member 36 punctured by the rear top portion 86 of the needle 58, fluid medicament 53 begins to flow through the needle. More specifically, the drive spring 116 pushes the plunger 46 forwardly within medicament cartridge 24, thereby forcing the fluid medicament 53 outwardly from the cartridge 24 and through the needle 58 into the injection site. The plunger 46 slidingly moves to the forwardmost position within the medicament cartridge 24 to substantially expel all of the fluid medicament 53 therein. It can be appreciated, however, that the distance between the front end of the collet 188 and the flange may have a shorter length such that the plunger does not move all the way forward inside the cartridge 24. This arrangement is preferred when it is desired to expel only a portion of the medicament 53 from the cartridge 24. For example, with Epinephrine it is desirable to have a cartridge with a 1 ml supply and the collet is configured to cause only 0.3 ml to be injected into the injection site. With expensive medicaments, however, it is more cost-effective to expel as much medicament as possible to avoid waste.

Figure 6:
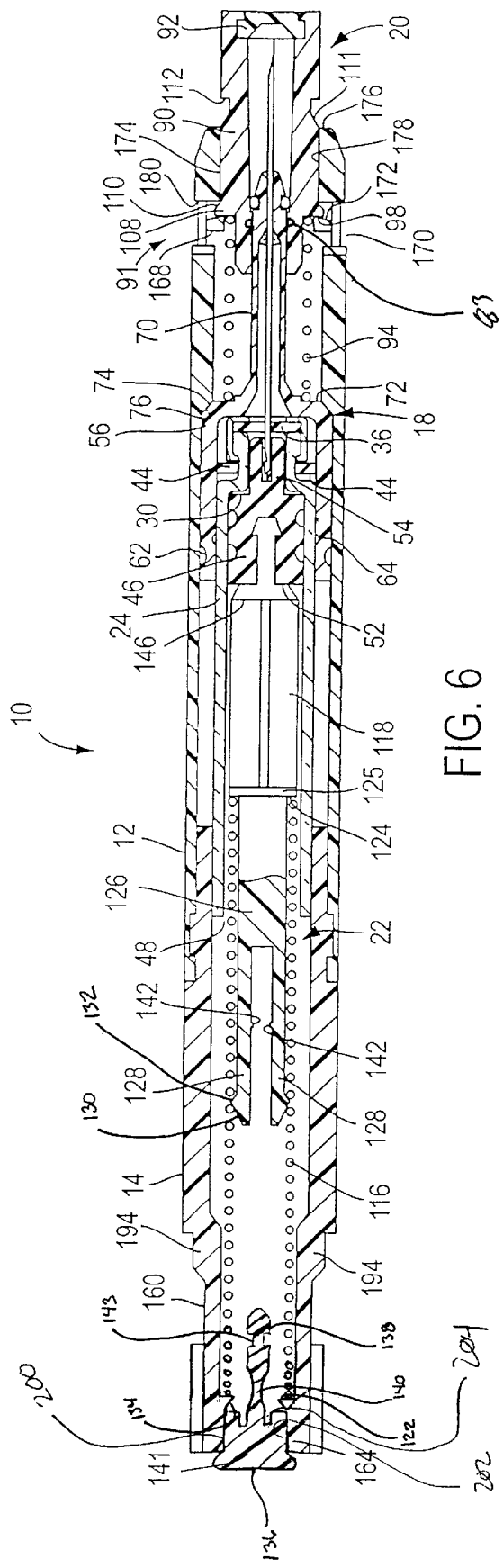
FIG. 6 is a longitudinal sectional view of the auto-injector of the present invention and illustrating the deployment of the needle cover after the user completes the injection.

As shown in FIG. 6, when the injector device 10 is removed from the injection site, the needle cover 90 is moved forwardly by the extension spring 94 into the protective position. More specifically, the needle cover extension spring 94 is compressed upon actuation of the injector device 10. The return spring 94 biases the needle cover 90 for forward movement, overcoming the finger snaps 168 retaining it within forward housing 12. However, while the user holds the injector device 10 against the injection site, the needle cover 90 remains in place. Once the injection device 10 is removed from the injection site, the extension spring 94 drives the needle cover 90 forwardly. The needle cover ridge 108 then slides past finger snaps 168, whereupon the locking surfaces 172 snap inwardly behind shoulder 98 so as to secure the needle cover 90 in the forwardly extending protective position. The needle cover 90 now projects forwardly beyond the forwardmost end 176 of the injector device 10, covering the forward portion of the needle 58 for disposal of the device.

Figure 11:
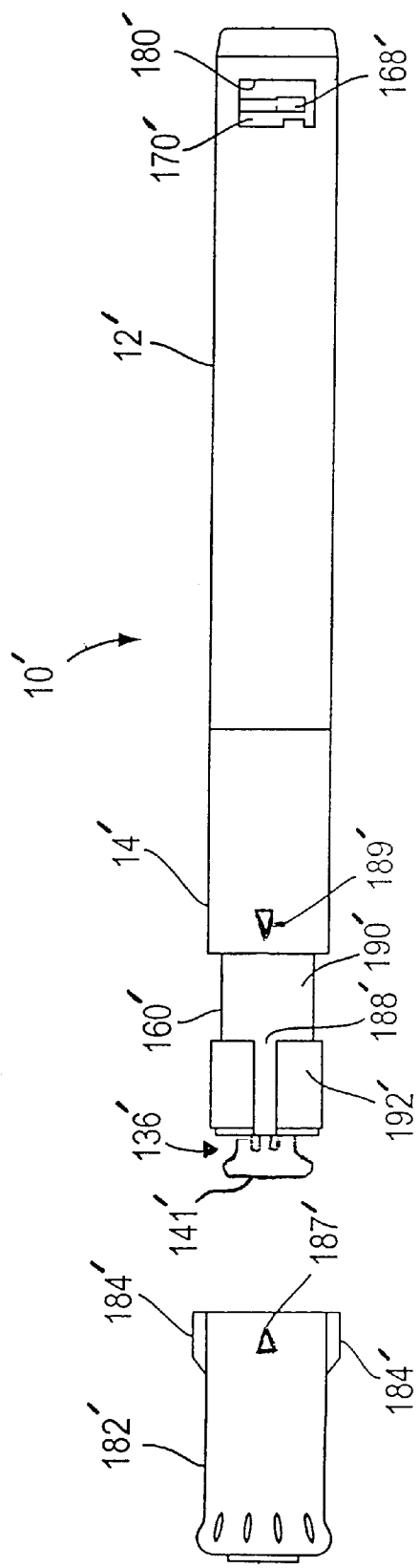
FIG. 11 is an elevated view of an alternative embodiment of an auto injector constructed in accordance with the principles of the present invention.

FIG. 11 shows an alternative embodiment of an auto-injector constructed in accordance with the principles of the present invention, generally indicated at 10'. The auto injector 10' is identical to the one shown in FIGS. 1–10, with certain exceptions. Thus, identical reference numerals marked in FIG. 11 as prime will correspond to the same features in the auto-injector of FIGS. 1–10. The main difference in this embodiment is that the movement limiting projections 194 have been removed so that deforming the cap 182' is not necessary for removal. This arrangement is preferable for injectors which are to be used by children or other people with low manual dexterity, such as arthritis sufferers.

Figure 12:
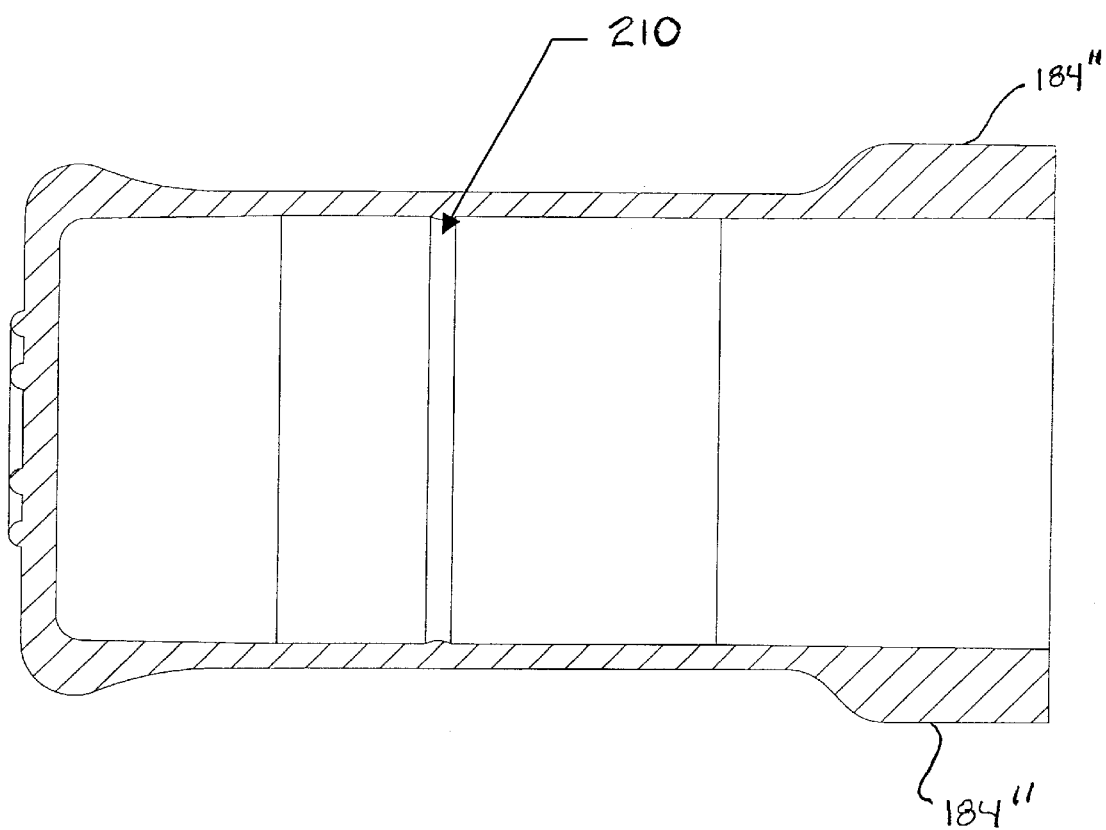
FIG. 12 shows an alternative cover.

FIG. 12 shows an alternative cover 182" that may be utilized in pace of covers 182 and 182'. The cover 182" has release portions 184" similar to the other covers dislclosed and includes an internal annular ridge 210. The housing rear end will have four arcuate ridge portions (not shown) spaced annularly about its exterior and an annular groove (not shown) is formed forwardly of the acrucate ridge portions. The cover is positioned on the rear end portion with the ridge 210 engaged in the groove. To cover 182" is removed by pulling axially rearwardly with sufficient force to cause the ridge 210 to ride up and over the arcuate ridge portions. The engagement between the groove and the ridge 210 is basically a detent relationship.

It can be appreciated that the auto-injector device 10, in accordance with the principles of the present invention, incorporates a needle cover assembly 20 that replaces the traditional needle sheath and provides rigid protection for the needle 58. It can also be understood that the rigid needle cover 90 encapsulates the forward end of the needle after an injection and prevents the user from seeing the needle 58 as it is withdrawn from the injection site. The needle cover 90 also locks in the extended protective position thereby preventing undesirable access to the needle 58 after an injection operation.

The activation pin 136 snap-fit interference with the resilient collet arms 128 provides for a controlled activation load which must be applied in order to actuate the auto-injection device 10.

As described, the needle 58 is sealed within the device 10 prior to use, to allow for post-assembly sterilization of medicament by means of autoclaving with a pressurized steam/air mixture. More specifically, the rubber washer 44, O-ring 82, and needle cover forward seal 92 isolate the needle 58 preventing moisture ingress into the needle area during sterilization. A secondary function of the rubber washer 44 is to provide a detent snap to keep the medicament cartridge 24 back prior to activation of the device, and to prevent the rear end 86 of the needle 58 separated from the forward cartridge seal 36 prior to activation of the device.

The foregoing preferred embodiments have been provided to illustrate the functional and structural principles of the present invention and are not intended to be limiting. To the contrary, the principles of the present invention are intended to encompass any and all modifications, substitutions, and alterations within the spirit and scope of the appended claims.

It should be noted that the appended claims are not phrased in the "means for performing a specified function" format permitted by 35 U.S.C. §112, paragraph 6. This is to make clear the intent that claims are not intended to be interpreted under §112, paragraph 6 so as to be limited solely to the structures disclosed in the present application and their equivalents.

Any U.S. patents or patent application mentioned hereinabove and not specifically incorporated by reference into the present application are hereby incorporated in their entirety into the present application by reference.

We claim:

1. An automatic injector comprising:

a housing having a longitudinal axis and opposed forward and rearward end portions, said forward end portion being engageable with a portion of flesh defining an injection site;

a needle having a forward lip portion, a rearward tip portion, and a fluid passageway formed therein open to said forward and rearward tip portions;

said needle being movable relative to said housing between (1) a normal, inoperative position wherein said needle is disposed entirely within said housing and (2) an injecting position wherein the forward tip portion of said needle extends forwardly of said housing forward end portion;

a medicament cartridge having a sealed interior containing a supply of fluid medicament;

said medicament cartridge being normally sealed from said needle, said medicament cartridge and said needle being constructed and arranged to be fluidly communicated during an automatic injecting operation such that the rearward tip portion of said needle pierces said cartridge and extends rearwardly into said cartridge interior so as to fluidly communicate the fluid passageway of said needle with said cartridge interior and allow the fluid medicament contained in said cartridge interior to flow into said fluid passageway;

a manually operable drive assembly having an actuator extending generally rearwardly from the rearward end portion of said housing, said drive assembly being constructed and arranged such that a user can perform the automatic injecting operation by engaging the forward end portion of said housing with the aforesaid injection site and manually operating said actuator such that said drive assembly moves said needle to said injecting position thereof and causes said cartridge and said needle to be fluidly communicated so that the forward tip portion of said needle pierces the injection site and the rearward tip portion of said needle pierces said cartridge, said drive assembly subsequently forcing the fluid medicament outwardly from said cartridge interior through the fluid passageway of said needle and into the injection site; and a removal resistant actuator cover positioned on the rearward end portion of said housing so as to cover said actuator and prevent unintended operation of said actuator, said cover having an annular wall portion made from yieldingly deformable material;

one of said actuator cover and said housing rearward end portion providing a generally radially extending locking projection and the other of said actuator cover and said housing rearward end portion having structure defining a generally radially extending shoulder surface and a generally axially extending groove open to said shoulder surface;

said cover and said housing rearward end portion being constructed and arranged such that said cover can be turned relative to said housing rearward end portion about the aforesaid longitudinal axis from (1) a removal resisting position wherein said locking projection and said groove are out of circumferential alignment with respect to one another so that said shoulder surface and said projection cooperate to prevent said cover from being moved axially outwardly relative to said housing rearward portion and (2) a removal allowing position wherein said locking projection and said groove are in substantial circumferential alignment with respect to one another so that said cover can be removed from said housing rearward portion by moving said cover axially outwardly relative to said housing rearward portion so as to expose said actuator and permit manual operation thereof;

said one of said cover and said housing rearward end portion having a movement limiting projection substantially circumferentially aligned with said groove, said actuator cover being constructed and arranged such that the user can manually deform said annular wall portion by applying manual pressure thereto so as to affect generally radial relative movement between said locking projection and said movement limiting projection from normal, locking positions to releasing positions;

said movement limiting projection being positioned and configured such that, when said locking projection and said movement limiting projection are in said locking positions thereof, said locking projection will engage said movement limiting projection as said cover is being turned toward said removal allowing position thereof to thereby prevent said cover from being turned into said removal allowing position, said movement limiting projection being positioned and configured such that, when said locking projection and said movement limiting projection are in said releasing positions thereof, said locking projection will pass over said movement limiting projection as said cover is being turned towards said removal allowing position thereof to thereby allow said cover to be turned into said removal allowing position.

2. An automatic injector according to claim 1, wherein said locking projection is provided on an interior surface of said actuator cover and wherein said movement limiting projection and said structure defining said shoulder surface and said groove is provided on said housing rear end portion.

3. An automatic injector according to claim 2, wherein said actuator cover further comprises a top wall portion integrally formed with said side wall portion.

4. An automatic injector according to claim 3, wherein said cover has a pair of said locking projections disposed approximately 180 degrees apart from one another and wherein said housing rearward end portion has a pair of said grooves disposed approximately 180 degrees apart from one another and a pair of said movement limiting projections disposed approximately 180 degrees apart from one another.

5. An automatic injector according to claim 2, wherein said housing rearward end portion has a housing-associated indication marking formed on an exterior surface thereof and said actuator cover has a cover-associated indication marking formed on an exterior surface thereof, said indication markings being positioned to be generally circumferentially aligned with one another when said actuator cover is in said removal allowing position thereof to thereby indicate to the user that said cover has been turned into said removal allowing position.

6. An automatic injector according to claim 5, wherein each of said indication markings is an arrow.

7. An automatic injector according to claim 2, further comprising a needle assembly comprising said needle and a needle carrier movable relative to said housing, said needle being fixedly mounted on said needle carrier, said needle assembly further comprising a substantially rigid, tubular protective needle cover and a cover extension spring disposed between said needle cover and said needle carrier, said needle cover having a substantially rigid tubular wall defining a forwardly facing needle passing aperture, said needle assembly being constructed and arranged such that, after drive assembly has caused said cartridge and said needle to fluidly communicated and moved said needle to said injecting position thereof, said cover extension spring resiliently extends as a result of the housing forward end portion being disengaged from the injection site so as to move said protective needle cover forwardly from an inoperative, retracted position to an extended needle protecting position wherein said needle passing aperture is disposed forwardly of the forward tip portion of said needle with said rigid tubular wall surrounding said needle in protecting relation.

8. An automatic injector according to claim 7, wherein said needle carrier has tubular cartridge mounting portion defining a rearwardly facing cartridge receiving opening, said cartridge mounting portion having an interior surface defining an annular groove, said cartridge having an annular sealing member fixedly secured thereto and being slidably movable relative to said needle carrier between (1) a normal, inoperative position wherein said cartridge is unpierced and disposed rearwardly of the rearward tip portion of said needle and (2) a medicament supplying position wherein said needle and said cartridge are fluidly communicated, said cartridge being received in said cartridge receiving opening with said sealing member thereof being removably received in said annular groove such that said sealing member and said annular groove cooperate to (1) substantially seal said rearwardly facing opening of said cartridge mounting portion and (2) prevent said cartridge from moving forwardly relative to said needle towards said medicament supplying position thereof before actuation of said drive assembly.

9. An automatic injector according to claim 8, wherein said interior surface of the cartridge mounting portion of said needle carrier has a plurality of generally axially extending grooves formed thereon, said generally axially extending grooves being positioned and configured to allow air to escape from the interior of said cartridge mounting portion around said sealing member as said cartridge is being moved forwardly to said medicament supplying position thereof to thereby prevent a pressure build-up within said carrier.

10. An automatic injector according to claim 9, wherein the cartridge mounting portion of said needle carrier has a rearwardly facing engaging surface and wherein said cartridge has a plunger slidably movably mounted in the interior thereof, said rearwardly facing engaging surface being positioned and configured such that a forwardly facing engaging surface of said cartridge engages said rearwardly facing engaging surface as said cartridge is being moved forwardly into said medicament supplying position thereof so as to prevent further relative forward movement of said cartridge with respect to said needle carrier, said drive assembly being constructed and arranged to move said plunger forwardly with respect to said cartridge after said cartridge has been moved into said medicament supplying position thereof so as to force the fluid medicament outwardly from said cartridge interior.

11. An automatic injector according to claim 10, wherein said needle carrier has a forwardly facing engaging surface and said protective needle cover has a rearwardly facing engaging surface, said needle assembly and said cartridge being constructed and arranged such that during said automatic injecting operation said drive assembly (1) drives said needle carrier and said cartridge together forwardly relative to said protective needle cover until said needle is moved into said injecting position thereof and the forwardly facing engaging surface of said needle carrier engages the rearwardly facing engaging surface of said needle cover so as to limit further relative forward movement of said needle carrier with respect to said needle cover, (2) then moves said cartridge forwardly into said medicament supplying position thereof until said forwardly facing engaging surface of said cartridge engages the rearwardly facing engaging surface of said needle carrier to prevent further relative forward movement of said cartridge with respect to said needle carrier and (3) thereafter moves said plunger forwardly relative to said cartridge so as to force the medicament outwardly from said cartridge interior through the fluid passageway of said needle.

12. An automatic injector according to claim 2, wherein the rearward end portion of said housing has an annular flange and rearwardly extending flange wherein said drive assembly comprises:

a collet having a pair of flexible arms, and an annular outwardly extending flange, said collet having a forward end portion engaged with said cartridge;

a compressed coil spring engaged with said inwardly extending flange and said outwardly extending flange;

said inwardly extending flange providing a rearwardly facing locking surface and said flexible arms having end portions providing forwardly facing locking surfaces, said locking surfaces being engaged to prevent said collet from moving forwardly with respect to said housing;

said actuator having a forward portion received between said flexible arms so as to prevent the end portions of said arms and an intermediate portion which is thinner than said forward portion;

said actuator being constructed and arranged such that manually moving said actuator forwardly allows the end portions of said flexible arms to collapse inwardly towards the thinner intermediate portion so that said locking surfaces disengage from one another to allow the spring to extend and drive said collet forwardly.

13. An automatic injector according to claim 1, wherein said cartridge has a forwardly facing opening and a pierceable cartridge sealing member sealing said forwardly facing opening, said cartridge being slidably movable between (1) a normal, inoperative position wherein said cartridge is unpierced and disposed rearwardly of the rearward tip portion of said needle and (2) a medicament supplying position wherein said needle and said cartridge are fluidly communicated.

14. An automatic injector comprising:

a housing having opposed forward and rearward end portions, said forward end portion being engageable with a portion of flesh defining an injection site;

a needle assembly comprising a needle carrier with a sterilized interior, a tubular substantially rigid protective needle cover with a sterilized interior, and a sterilized needle mounted within said needle carrier, said needle having a forward tip portion, a rearward tip portion, and a fluid passageway formed therein open to said forward and rearward tip portions;

said needle cover having a substantially rigid tubular wall defining a forwardly facing needle passing opening and a rearwardly facing needle carrier receiving opening, said needle carrier and said needle being mounted within said needle carrier receiving opening;

said needle carrier being movable relative to said housing and said protective needle cover between (1) a normal, inoperative position wherein said needle is disposed entirely within said housing and said needle cover and (2) an injecting position wherein the forward tip portion of said needle extends forwardly of said housing forward end portion through the needle passing opening in said protective needle cover;

said needle assembly further comprising a first sealing member substantially sealing said needle passing opening when said needle carrier is in said inoperative position thereof and a second sealing member having an annular shape and being disposed between said needle carrier and said needle cover so as to substantially seal the needle guide receiving opening of said needle cover when said needle carrier is in said inoperative position thereof;

a medicament cartridge having a sealed interior containing a supply of fluid medicament, said needle carrier having a tubular cartridge mounting portion defining a rearwardly facing opening and said cartridge being mounted to said cartridge mounting portion of said needle carrier;

said medicament cartridge being normally sealed from said needle, said medicament cartridge and said needle being constructed and arranged to be fluidly communicated during an automatic injecting operation such that the rearward tip portion of said needle pierces said cartridge and extends rearwardly into said cartridge interior so as to fluidly communicate the fluid passageway of said needle with said cartridge interior and allow the fluid medicament contained in said cartridge interior to flow into said fluid passageway;

a third sealing member having an annular shape and being disposed between said tubular cartridge mounting portion of said needle carrier and said cartridge so as to substantially seal the rearwardly facing opening of said cartridge mounting portion when said cartridge is in said inoperative position thereof;

said first sealing member, said second sealing member and said third sealing member cooperating with the sterilized interior of said needle cover and the sterilized interior of said needle carrier to define a substantially sealed sterilized needle chamber with said sterilized needle disposed therein such that unsterilized ambient air is prevented from entering said needle chamber and contaminating either said needle or said chamber;

a manually operable drive assembly having an actuator extending generally rearwardly from the rearward end portion of said housing, said drive assembly being constructed and arranged such that a user can perform the automatic injecting operation by engaging the forward end portion of said housing with the aforesaid injection site and manually operating said actuator such that said drive assembly moves said needle to said injecting position thereof and causes said cartridge and said needle to be fluidly communicated so that the forward tip portion of said needle pierces the injection site and the rearward tip portion of said needle pierces said cartridge, said drive assembly subsequently forcing the fluid medicament outwardly from said cartridge interior through the fluid passageway of said needle and into the injection site.

15. An automatic injector according to claim 14, wherein a forward end portion of said cartridge is slidably mounted within said cartridge mounting portion such that said cartridge is movable relative to said needle between (1) a normal, inoperative position wherein said cartridge is unpierced and disposed rearwardly of the rearward tip portion of said needle and (2) a medicament supplying position wherein said cartridge is moved forwardly of said inoperative position thereof such that the rearward tip portion of said needle pierces said cartridge and extends into the cartridge interior so that said cartridge and said needle are fluidly communicated.

16. An automatic injector according to claim 15, wherein the interior surface of said cartridge mounting portion has a generally axially extending groove formed thereon and wherein said third sealing member is fixedly mounted to said cartridge, said generally axially extending groove being positioned and configured to allow air to escape from the sterilized interior of said cartridge mounting portion around said third sealing member as said cartridge is being moved forwardly to said medicament supplying position thereof to thereby prevent a pressure build-up within said needle carrier.

17. An automatic injector according to claim 16, wherein the interior surface of said cartridge mounting portion has an annular groove formed thereon, said annular third sealing member being removably received in said annular groove when said cartridge is in said inoperative position thereof such that said third sealing member and said groove cooperate to prevent said cartridge from moving forwardly relative to said needle toward said medicament supplying position thereof before activation of said drive assembly.

18. An automatic injector according to claim 17, wherein said needle carrier has a forward end portion with an exterior surface having an annular groove formed thereon, said annular second sealing member being fixedly mounted in said annular groove of the needle carrier forward end portion.

19. An automatic injector according to claim 14, wherein the rearward end portion of said housing has an annular flange and rearwardly extending flange wherein said drive assembly comprises:

a collet having a pair of flexible arms, and an annular outwardly extending flange, said collet having a forward end portion engaged with said cartridge;

a compressed coil spring engaged with said inwardly extending flange and said outwardly extending flange;

said inwardly extending flange providing a rearwardly facing locking surface and said flexible arms having end portions providing forwardly facing locking surfaces, said locking surfaces being engaged to prevent said collet from moving forwardly with respect to said housing;

said actuator having a forward portion received between said flexible arms so as to prevent the end portions of said arms and an intermediate portion which is thinner than said forward portion;

said actuator being constructed and arranged such that manually moving said actuator forwardly allows the end portions of said flexible arms to collapse inwardly towards the thinner intermediate portion so that said locking surfaces disengage from one another to allow the spring to extend and drive said collet forwardly.

20. An automatic injector according to claim 14, wherein said third sealing member is a rubber washer.

21. An automatic injector according to claim 14, wherein said second sealing member is an O-ring.

22. An automatic injector according to claim 14, further comprising:

a removal resistant actuator cover positioned on said rearward end portion of said housing so as to cover said actuator and prevent unintended operation of said actuator;

one of said actuator cover and said housing rearward end portion providing a generally radially extending locking projection and the other of said actuator cover and said housing rearward end portion having structure defining a generally radially extending shoulder surface and a generally axially extending groove open to said shoulder surface;

said cover and said housing rearward end portion being constructed and arranged such that said cover can be turned relative to said housing rearward end portion about a longitudinal axis of said housing from (1) a removal resisting position wherein said locking projection and said groove are out of circumferential alignment with respect to one another so that said cover can be removed from said housing rearward end portion by moving said cover axially outwardly relative to said housing rearward end portion so as to expose said actuator and permit manual operation thereof.

23. An automatic injector according to claim 14, wherein said needle assembly further comprises a cover extension spring disposed between said needle cover and said needle carrier, said needle assembly being constructed and arranged such that, after drive assembly has caused said cartridge and said needle to be fluidly communicated and moved needle to said injecting position thereof, said cover extension spring resiliently extends as a result of the housing forward end portion being disengaged from the injection site so as to move said needle cover forwardly from an inoperative, retracted position to an extended needle protecting position wherein said needle passing opening is disposed forwardly of the forward tip portion of said needle with said rigid tubular wall surrounding said needle in protecting relation.

24. An automatic injector comprising:

a housing having opposed forward and rearward end portions, said forward end portion being engageable with a portion of flesh defining an injection site;

a needle assembly comprising a needle carrier with a sterilized interior, and a sterilized needle mounted within said needle carrier, said needle having a forward tip portion, a rearward tip portion, and a fluid passageway open to both said forward and rearward tip portions;

said needle carrier being movable relative to said housing between (1) a normal, inoperative position wherein said needle is disposed entirely within said housing and (2) an injecting position wherein the forward tip portion of said needle extends forwardly of said forward end portion;

said needle assembly comprising sealing structure substantially sealing a forward portion of said needle carrier and the forward tip portion of said needle;

a medicament cartridge having a sealed interior containing a supply of fluid medicament;

said needle carrier having a tubular cartridge mounting portion defining a rearwardly facing opening, said cartridge being slidably mounted to said cartridge mounting portion of said needle carrier;

said medicament cartridge being movable relative to said needle between (1) a normal, inoperative position wherein said cartridge is unpierced and disposed rearwardly of the rearward tip portion of said needle and (2) a medicament supplying position wherein said cartridge is moved forwardly of said inoperative position thereof such that the rearward tip portion of said needle pierces said cartridge and extends rearwardly into said cartridge interior so as to fluidly communicate the fluid passageway of said needle with said cartridge interior and allow the fluid medicament contained in said cartridge interior to flow into said fluid passageway;

an annular sealing member disposed between said cartridge and said cartridge mounting portion of needle carrier so as to substantially seal the rearwardly facing opening of said cartridge mounting portion when said cartridge is in said inoperative position thereof;

said sealing structure and said sealing member cooperating with the sterilized interior of said needle carrier to define a substantially sealed sterilized needle chamber with said needle disposed therein such that unsterilized ambient air is prevented from entering said needle chamber and contaminating either said needle or said chamber when both said needle carrier and said cartridge are in the inoperative positions thereof;

said tubular cartridge mounting portion having at least one generally axially extending groove formed thereon, said groove being positioned and configured to allow air to escape from the sterilized interior of said cartridge mounting portion as said cartridge is being moved forwardly to said medicament supplying position thereof to thereby prevent a pressure build-up in said cartridge mounting portion;

a manually operable drive assembly having an actuator extending generally rearwardly from the rearward end portion of said housing, said drive assembly being constructed and arranged such that a user can perform an automatic injecting operation by engaging the forward end portion of said housing with the aforesaid injection site and thereafter manually operating said actuator such that said drive assembly moves both said needle carrier to said injecting position thereof and said cartridge to said medicament supplying position thereof so that the forward tip portion of said needle pierces the injection site and the rearward tip portion of said needle pierces said cartridge and then said drive assembly forces the fluid medicament outwardly from said cartridge interior through the fluid passageway of said needle and into the injection site.

25. An automatic injector according to claim 24, wherein said needle assembly further comprises a tubular substantially rigid protective needle cover with a sterilized interior, said needle cover having a substantially rigid tubular wall defining a forwardly facing needle passing opening and a rearwardly facing needle carrier receiving opening, said needle carrier and said needle being mounted within said needle carrier receiving opening;

said sealing structure comprising a first sealing member substantially sealing said needle passing opening when said needle carrier is in said inoperative position thereof and a second sealing member having an annular shape and being disposed between said needle carrier and said needle cover so as to substantially seal the needle carrier receiving opening of said needle cover when said needle carrier is in the inoperative position thereof;

said first sealing member, said second sealing member, and said sealing member disposed between said cartridge and said cartridge mounting portion cooperating to define said substantially sealed sterilized needle chamber.

26. An automatic injector according to claim 24, wherein said cartridge is received within said rearwardly facing opening of said cartridge mounting portion and wherein said groove is formed on an interior surface of said cartridge mounting portion.

27. An automatic injector according to claim 24, wherein said cartridge mounting portion has an annular groove formed thereon, said sealing member being removably received in said annular groove when said cartridge is in said inoperative position thereof such that said sealing member and said groove cooperate to prevent said cartridge from moving forwardly relative to said needle toward said medicament supplying position thereof before operation of said drive assembly.

28. An automatic injector according to claim 24, wherein said sealing member is a rubber washer.

29. An automatic injector according to claim 25, wherein said second sealing member is an O-ring.

30. An automatic injector according to claim 24, wherein said needle assembly further comprises a cover extension spring disposed between said needle cover and said needle carrier, said needle assembly being constructed and arranged such that, after both said cartridge has been moved to said medicament supplying position thereof and said needle has been moved to said injecting position thereof, said cover extension spring resiliently extends as a result of the housing forward end portion being disengaged from the injection site so as to move said needle cover forwardly from an inoperative, retracted position to an extended needle protecting position wherein said needle passing opening is disposed forwardly of the forward tip portion of said needle with said rigid tubular wall surrounding said needle in protecting relation.

31. An automatic injector comprising:

a housing having opposed forward and rearward end portions, said forward end portion being engageable with a portion of flesh defining an injection site;

a needle having a forward tip portion, a rearward tip portion, and a fluid passageway formed therein open to said forward and rearward tip portions;

said needle being movable relative to said housing between (1) a normal, inoperative position wherein said needle is disposed entirely within said housing and (2) an injecting position wherein the forward tip portion of said needle extends forwardly of said housing forward end portion;

a medicament cartridge having a sealed interior containing a supply of fluid medicament;

said medicament cartridge being normally sealed from said needle, said medicament cartridge and said needle being constructed and arranged to be fluidly communicated during an automatic injecting operation such that the rearward tip portion of said needle pierces said cartridge and extends rearwardly into said cartridge interior so as to fluidly communicate the fluid passageway of said needle with said cartridge interior and allow the fluid medicament contained in said cartridge interior to flow into said fluid passageway;

a manually operable drive assembly having an actuator extending generally rearwardly from the rearward end portion of said housing, said drive assembly being constructed and arranged such that a user can perform the automatic injecting operation by engaging the forward end portion of said housing with the aforesaid injection site and manually operating said actuator such that said drive assembly both moves said needle to said injecting position thereof and causes said cartridge and said needle to be fluidly communicated so that the forward tip portion of said needle pierces the injection site and the rearward tip portion of said needle pierces said cartridge, said drive assembly subsequently forcing the fluid medicament outwardly from said cartridge interior through the fluid passageway of said needle and into the injection site;

said actuator having (1) a head with an exterior side surface, and (2) a forward portion spaced forwardly from said head, and (3) an intermediate portion extending between said forward portion and said head;

said housing rearward end portion having (1) a first interior surface defining a forward portion receiving space and (2) a second interior surface defining an actuator head receiving space, said forward portion being received in said forward portion receiving space such that said first interior surface supports said forward portion against radial bending with said intermediate portion extending rearwardly away from said forward portion receiving opening and being radially unsupported, said exterior side surface and said second interior surface of said housing rearward end portion being positioned and configured such that a portion of said actuator head is received within said actuator head receiving space with said exterior side surface of said actuator head facing said second interior surface of said housing rearward end portion in closely spaced relation so as to limit radial movement of said head to thereby substantially prevent radial bending of said intermediate portion.

32. An automatic injector according to claim 31, wherein said exterior side wall surface of said actuator head is generally cylindrical and wherein said actuator head receiving opening is generally cylindrical.

33. An automatic injector according to claim 31, further comprising:

a removal resistant actuator cover positioned on said rearward end portion of said housing so as to cover said actuator and prevent unintended operation of said actuator;

one of said actuator cover and said housing rearward end portion providing a generally radially extending locking projection and the other of said actuator cover and said housing rearward end portion having structure defining a generally radially extending shoulder surface and a generally axially extending groove open to said shoulder surface;

said cover and said housing rearward end portion being constructed and arranged such that said cover can be turned relative to said housing rearward end portion about a longitudinal axis of said housing from (1) a removal resisting position wherein said locking projection and said groove are out of circumferential alignment with respect to one another so that said cover can be removed from said housing rearward end portion by moving said cover axially outwardly relative to said housing rearward end portion so as to expose said actuator and permit manual operation thereof.

34. An automatic injector comprising:

a housing having opposed forward and rearward end portions, said forward end portion being engageable with a portion of flesh defining an injection site;

a needle having a forward tip portion, a rearward tip portion, and a fluid passageway formed therein open to said forward and rearward tip portions;

said needle being movable relative to said housing between (1) a normal, inoperative position wherein said needle is disposed entirely within said housing and (2) an injecting position wherein the forward tip portion of said needle extends forwardly of said housing forward end portion;

a medicament cartridge having a sealed interior containing a supply of fluid medicament;

said medicament cartridge being normally sealed from said needle, said medicament cartridge and said needle being constructed and arranged to be fluidly communicated during an automatic injecting operation such that the rearward tip portion of said needle pierces said cartridge and extends rearwardly into said cartridge interior so as to fluidly communicate the fluid passageway of said needle with said cartridge interior and allow the fluid medicament contained in said cartridge interior to flow into said fluid passageway;

a manually operable drive assembly having an actuator extending generally rearwardly from the rearward end portion of said housing, said drive assembly being constructed and arranged such that a user can perform the automatic injecting operation by engaging the forward end portion of said housing with the aforesaid injection site and manually operating said actuator such that said drive assembly both moves said needle to said injecting position thereof and causes said cartridge and said needle to be fluidly communicated so that the forward tip portion of said needle pierces the injection site and the rearward tip portion of said needle pierces said cartridge, said drive assembly subsequently forcing the fluid medicament outwardly from said cartridge interior through the fluid passageway of said needle and into the injection site;

said actuator having, (1) a head with an exterior side surface, (2) a forward portion spaced forwardly from said head, and (3) an intermediate portion extending between said forward portion and said head, said intermediate portion being thinner than said forward portion;

the rearward end portion of said housing having (1) an interior surface defining an actuator head receiving space and (2) an inwardly extending flange;

said drive assembly comprising:

a collet having a pair of flexible arms, and an outwardly extending flange, said collet having a forward end portion engaged with said cartridge;

a compressed coil spring engaged with said inwardly extending flange of the rearward end portion of the housing and said outwardly extending flange of the collet;

said inwardly extending flange providing a rearwardly facing locking surface and said flexible arms having end portions providing forwardly facing locking surfaces, said locking surfaces being engaged to prevent said collet from moving forwardly with respect to said housing;

said forward portion of said actuator being received between said flexible arms so as to prevent inward movement of the end portions of said arms, and said intermediate portion of said actuator extending rearwardly away from said forward portion and said end portions of said arms;

said actuator being constructed and arranged such that manually moving said actuator forwardly allows the end portions of said flexible arms to collapse inwardly towards the thinner intermediate portion so that said locking surfaces disengage from one another to allow the spring to extend and drive said collet forwardly;

said exterior side surface of said head and said interior surface of said housing rearward end portion being positioned and configured such that a portion of said actuator head is received within said actuator head receiving space with said exterior side surface of said actuator head facing said interior surface of said housing rearward end portion in closely spaced relation so as to limit radial movement of said head to thereby substantially prevent radial bending of said intermediate portion.

35. A method for assembling an automatic injector comprising:

providing a medicament cartridge with a sealed interior containing a supply of fluid medicament;

providing a sterilized needle and a needle carrier with a sterilized interior, said needle being mounted to said needle carrier and having forward and rearward tip portions and a fluid passageway open to said forward and rearward tip portions, said needle carrier having a tubular cartridge mounting portion defining a rearwardly facing opening;

providing a substantially rigid tubular needle cover with a sterilized interior, a forwardly facing needle passing opening, and a rearwardly facing needle carrier receiving opening, said needle cover having a first sealing member substantially sealing said needle passing opening;

providing a second sealing member;

mounting said needle carrier with said needle mounted thereon to said needle cover in a sterilized area by positioning a forward end portion of said needle carrier within said needle carrier receiving opening with said second sealing member disposed between said needle carrier forward end portion and said needle cover such that said second sealing member substantially seals said needle carrier receiving opening;

providing a medicament cartridge with a sealed interior containing a supply of fluid medicament;

providing a third sealing member;

mounting said cartridge to said cartridge mounting portion of said needle carrier with said third sealing member disposed therebetween in said sterilized area such that said third sealing member substantially seals rearwardly facing opening of said cartridge mounting portion, wherein said first sealing member, said second sealing member, and said third sealing member cooperate with the sterilized interior of said needle carrier and the sterilized interior of said needle cover to define a substantially sealed sterilized needle chamber with said sterilized needle disposed therein such that sterilized ambient air is prevented from entering said needle chamber and contaminating either said needle or said chamber, said needle carrier with said needle mounted thereto, said needle cover, and said cartridge defining a needle and cartridge assembly when mounted together as aforesaid;

thereafter providing a housing and a manually operable drive assembly; and then positioning both said drive assembly and said needle and cartridge assembly together within said housing.

36. A method according to claim 35, wherein said act of mounting said needle carrier to said needle cover includes positioning a cover extension spring between said cover and said carrier.

37. A method according to claim 35, wherein said second sealing member is an O-ring.

38. A method according to claim 35, wherein said third sealing member comprises a rubber washer.

39. A method according to claim 35, wherein said act of mounting said cartridge to said cartridge mounting portion of said needle carrier includes mounting said third sealing member to a forward end portion of said cartridge and then inserting said forward end portion of said cartridge into said rearwardly facing opening of said cartridge mounting portion.

* * * * *